United States Patent
Delhom Munoz et al.

(10) Patent No.: US 9,119,709 B2
(45) Date of Patent: Sep. 1, 2015

(54) INTRASTOMAL SEGMENT

(75) Inventors: Salvador Gabriel Delhom Munoz, Parque Tecnologico (ES); Pere Manel Del Campo Garcia, Parque Tecnologico (ES); Rafael Ignacio Barraquer Copte, Parque Tecnologico (ES)

(73) Assignee: IMEX CLINIC, S.L., Parque Technologico, Paterna (Valencia) (ES)

( * ) Notice: Subject to any disclaimer, the term of this patent is extended or adjusted under 35 U.S.C. 154(b) by 0 days.

(21) Appl. No.: 14/119,717

(22) PCT Filed: May 25, 2012

(86) PCT No.: PCT/ES2012/070383
§ 371 (c)(1),
(2), (4) Date: Nov. 22, 2013

(87) PCT Pub. No.: WO2012/160237
PCT Pub. Date: Nov. 29, 2012

(65) Prior Publication Data
US 2014/0107778 A1    Apr. 17, 2014

(30) Foreign Application Priority Data
May 26, 2011  (ES) .................................. 201130857

(51) Int. Cl.
*A61F 2/14* (2006.01)

(52) U.S. Cl.
CPC ....................................... *A61F 2/147* (2013.01)

(58) Field of Classification Search
USPC ................................. 623/5.11–5.12
See application file for complete search history.

(56) References Cited

U.S. PATENT DOCUMENTS

| 5,405,384 | A | 4/1995 | Silvestrini |
| 5,888,243 | A | 3/1999 | Silvestrini |
| 5,944,752 | A | 8/1999 | Silvestrini |
| 6,096,076 | A | 8/2000 | Silvestrini |
| 6,138,307 | A | 10/2000 | McDonald |
| 6,214,044 | B1 | 4/2001 | Silvestrini |
| 6,966,927 | B1 | 11/2005 | Silvestrini |
| 2007/0219631 | A1 | 9/2007 | Chapoy et al. |
| 2009/0306774 | A1 * | 12/2009 | Park .............................. 623/6.38 |
| 2010/0286770 | A1 | 11/2010 | Tomalla et al. |

FOREIGN PATENT DOCUMENTS

| ES | 2133411 | 9/1999 |
| ES | 2134268 | 10/1999 |
| WO | 2009/079726 | 7/2009 |

* cited by examiner

*Primary Examiner* — David H Willse
*Assistant Examiner* — Tiffany Shipmon
(74) *Attorney, Agent, or Firm* — Greenblum & Bernstein P.L.C.

(57) ABSTRACT

A description has been provided herein of an intrastromal segment especially designed for use as a prosthesis inside the corneal tunnel of patients suffering from keratoconus. The segment consists of a lengthened body of variable dimensions in the form of an arc with noticeably rounded ends, devoid of any communicating orifice, and endowed with a transverse section that may be triangular, trapezoidal, hexagonal or oval, with at least three marks connecting to the narrowest side for which two ends aid the safe handling of the segment and the mid-section mark serves as a positional reference point. The segment will be connected to a disposable guide track along which it moves and from which it is pushed into the implantation position.

8 Claims, 2 Drawing Sheets

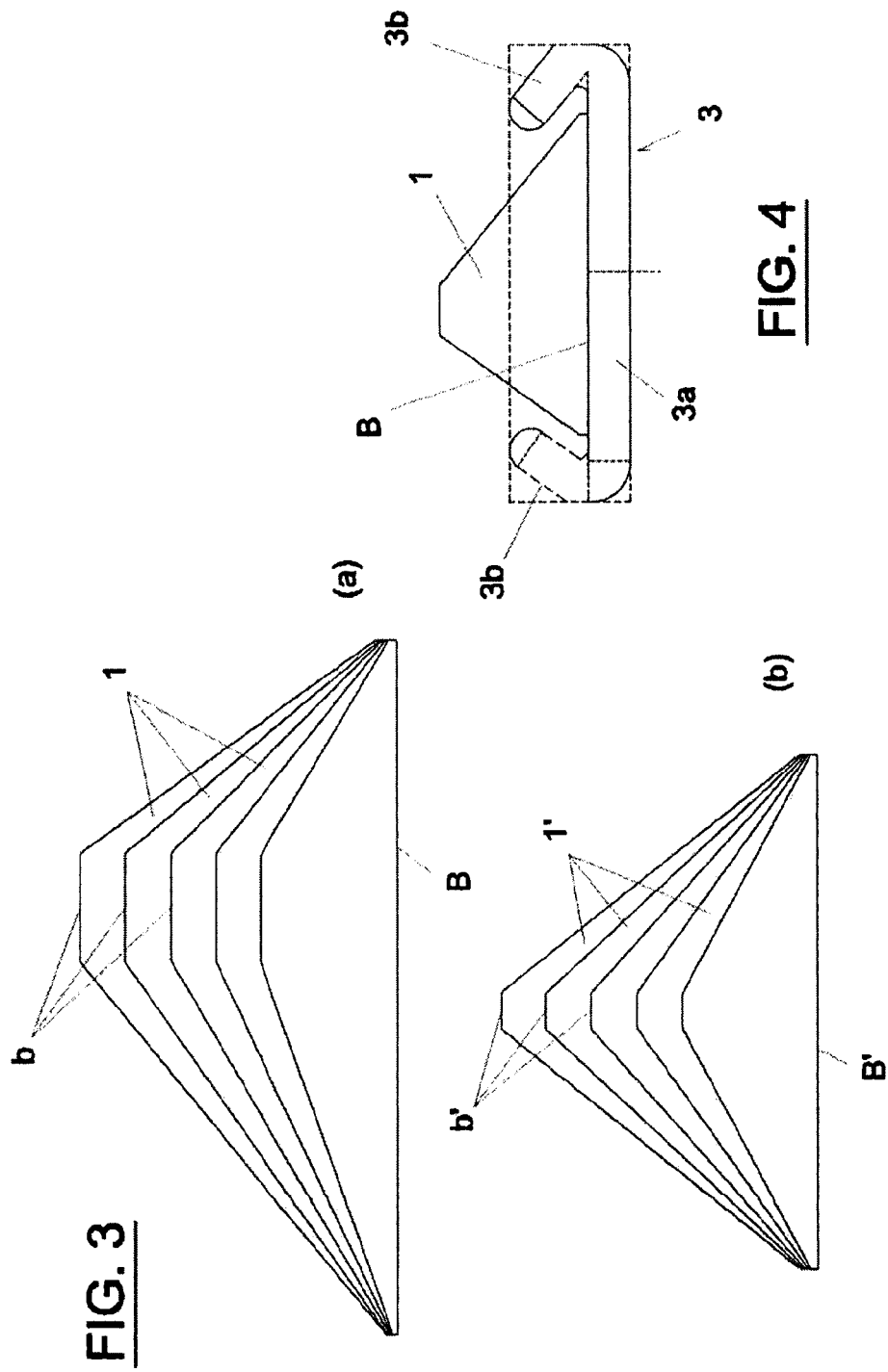

INTRASTOMAL SEGMENT

OBJECT OF THE INVENTION

The present invention consisting of an intrastromal segment has essential new characteristics and significant advantages over current methods to achieve the same goals available through existing technology.

More specifically, the invention develops an intrastromal segment especially designed for use as a positional prosthesis on the inside of the intrastromal tunnel with the aim of treating patients afflicted with keratoconus. The segment part of the invention consists of a longitudinal body, lengthened into a generally arc-shaped configuration positioned across from equidistant segments of the aforementioned body which have rounded closed ends with marks on the upper side to facilitate the correct positioning of the main segment, and one of which, (usually the centre mark) serves as a symmetrical reference point for the longitude of the arc; moreover, the segment includes a disposable guide/conduit medium inside of which the main segment can be positioned so that when the segment is inside the guide track, it is then ready to be implanted and can be manipulated with greater ease.

This invention falls within the industrial sector application field dedicated in particular to the manufacture of prostheses for the treatment of keratoconus in the cornea.

BACKGROUNDS

Experts in the area are familiar with the large number of people who are affected by a cornea pathology known as keratoconus. The term "keratoconus" is derived from two Greek terms "kerato" (cornea) and "konos" (cone). It is a condition in which the normal shape of the cornea is distorted and develops a deformation in the shape of a cone that changes and progressively alters the patient's vision, making it ever more blurry. The disease process depends on the age of the patient and the onset of symptoms. Normally, the younger the patient and more precipitous the onset of keratoconus symptoms occurs, the more rapid the progress; it always presents bilaterally and asymmetrically, either owing to congenital alterations or provoked through weakness in the corneal tissue (corneal surgery or previous trauma).

In the present day different treatment modalities are known, depending on the degree and corneal deformation process, these are listed here below:
  glasses in the early stages
  contact lenses if glasses are no longer effective
  intracorneal rings when the eye develops an intolerance for contact lenses and there is evidence of disease progression
  Cross-linking, or ultraviolet light treatment to halt the progress of keratoconus
  corneal transplant in more advanced stages of keratoconus and in cases where other options do not offer any hope of improvement (for example, corneal scarring, and very advanced keratoconus).

Exactly as has been shown, in the early stages the patient can use glasses. Nevertheless, when the disease progresses, the narrowing and deformation of the cornea causes a high irregular stigmatism that cannot be treated with glasses. In these cases it is important to use hard contact lenses that improve vision even if they do not halt the progression of the keratoconus, making surgery the only option for stopping the progressive deformation of the cornea. Cross-linking treatment is effective in stopping the evolution of keratoconus, can still be used in cases where there is good corneal thickness.

In light of this, determined implantable prostheses have been developed to be used in those cases where the disease has progressed to the point where the treatments discussed earlier are effective; these prostheses achieve many more practical outcomes for the patient. These prostheses consist of longitudinal segments in arc configurations that are implanted by using intrastromal tunnels both to guide the segments and for those that are affixed. These tunnels vary as much in width as in internal and external diameter, depending on the characteristics of the prosthesis.

At present, four design types of implants are used:
  triangular section segments: a section in the form of an isosceles triangle with different arc longitudes and thicknesses.
  trapezoid section segments: a section in the form of a triangle truncated at the top;
  hexagonal section segments: a section with six corners and
  oval section segments: a transverse section with oval configuration In all cases the previously mentioned segments that use current techniques, longitudinal arched bodies have openings that facilitate the insertion of a segment inside the corneal tunnel by use of a Sinskey hook. The elasticity of corneal tissue tends to cause problems with segment implantation. Additionally, segment manufacture uses milling and the material used is PMMA (polymethacrylate), without external buffing which means that the quality of the finished product is determined by the wear of the diamond tool that is used.

All this, together with the limitations of the software used in manufacture, makes the mechanization of the segment difficult, some of which are the following:
  fractures during handling;
  deposit of materials on the inside of the hole and consequent infection risk.
  Need to use Sinskey Hooks: risk of scratching the intrastromal layers and causing infections
  poor angulation for an easy implantation of the segment.
Milling of PPMA:
  The excessive use of the diamond produces poor finished products with risks of fracture or deposits with consequent infection risks.
Software Limitations:
  Impossibility of using free software that permits the production of all segments desired.

There are two established techniques for manufacturing intrastromal tunnels: manual and laser. Manual technique employs various instrumental tunnelizing materials manufactured in titanium and a diamond knife. The tunnelizing instruments do not so much cut as they delaminate intrastromally to create a tunnel, which incurs a high risk of perforation and in some cases requires the use of a suction console to keep the eye in a fixed position while the tunnel is being created. Complications that can arise with the manual technique are wide incisions, infections, tunnel asymmetry, deposits in the tunnel and post-operative trauma, among others.

In the case of femtosecond laser techniques, the laser provides pulses of intrastromal energy that causes a separation of the lamellae and creates a tunnel and the prosthesis entry incision. This technique provides several advantages over the manual technique since it is more sterile, less traumatic, provides exact depth without diameter limitation and less post-operative trauma among others.

When the possibilities offered by existing technology as covered in this brief commentary are taken into account, and the characteristics identified with each one, the present invention has as its primary objective the development and creation of an intrastromal segment for implantation in intrastromal tissue, concretely in the patient's cornea, through exclusive application of laser technology that allows us to eliminate at least a good part of the inconveniences and disadvantages that have been outlined above, and that implements a surgery that is the least traumatic possible, and with the least possible risk of causing complications. This goal is fully realized in the intrastromal segment that will be the described in what follows, whose principal characteristics appear summarized in the features portion of claim 1 annex.

In essence, the intrastromal segment proposed by the invention is conceived of as a longitudinally elongated body of variable dimensions according to each concrete need, designed for implantation by means designed for use with it. In contrast to known techniques, the segment of the present invention offers a configuration of noticeably rounded hubs devoid of any communicating openings that facilitate placement, with the consequent elimination of complications posed by these openings (see above discussion), and which also incorporates marks on one of their bases, optimally three marks on the narrowest base that allow correct positioning of the segment, and of these the centre mark is used as a reference point to know where the segment should go and when it is in position, thus also acting as a symmetrical reference point for the arc longitude. Additionally, and to avoid losing the segment or inverting it, the segment is put into place using a disposable implantation guide, but usable during the implantation stage, which connection allows the segment to be readied for implantation.

In this way, although with the use of laser techniques for creating the tunnel, segment tunnel implantation using the former techniques requires breaking the insertion process down into a series of phases that include a) in case where forceps are used, the extraction of the segment from the case, which already causes a certain level of difficulty owing to the form of the sections of the main segment (triangular, trapezoidal, hexagonal, oval) and therefore correspondingly demands an increased level of precaution and care; to introduce the segment with forceps through the incision with special care in cases of very thin segments to avoid inverted positioning of it that causes bad vision and should require new surgery; to open the incision and introduce the segment without causing it to move or jump in such a way as to position itself in the cornea with risk of infection, or causing deposits in the segment; it must be introduced entirely with tweezers while avoiding any movement of the patient's eye to keep the segment from jumping thereby requiring the surgery to be redone and in so doing creating additional risk of leaving deposits that could produce an infection or difficulty in introducing the segment into the tunnel in the case in which small fibres interpose themselves inside of the bridge, which would require the prosthesis to be removed and the bridge to be smoothed with the help of the tunnelling instrument, or of manual surgery for the posterior reintroduction of the segment, with the consequent traumatisation and stress on the cornea owing to the location and the force entailed, or (b) in the case where segment tunnel implantation is envisioned using a Sinskey hook, consistent in one instrumental piece that is introduced through the opening in the segment and finishes by implanting it, in which case the segment should be distanced from the incision to avoid risks of infections and that the incision might seal over in the future. The hook should be equipped with a titanium tip, not rounded, but sharp, which may result in trauma to the cornea if scratching should occur to the tissue, and which has the disadvantage that the segments must be handled by the openings themselves which are weak and may break when handled with the hook, requiring it to be replaced by a new one if it has not yet been introduced, and if it has, requiring a new incision to be made from the opposite side that would allow it to be handled. Each new incision would, of course, entail risks of perforation and infection, a danger that the invention segment avoids completely due to the formal and structural characteristics found in the disposable positioner (disposable guide track) that has been conceptualized and described in the preceding, and to the instrumental developed for an efficient handling of the segment, in particular the implanting mechanism that substitutes efficiently for the present methods, (and which is the object of a separate registration under the title of the same applicant).

BRIEF DESCRIPTION OF THE DRAWINGS

These and other features and advantages of the invention will be made more clear in the detailed description that follows an example of the preferred method of insertion provided solely by illustration and not limited, with reference to the accompanying illustrations, in which:

FIG. 3 illustrates schematized representations (a and b) of the raised ends of the segment invention, of the trapezoidal section, along with variables that account for its dimensions of width, and height.

FIG. 4 is a schematic illustration of the raised end of a segment inserted in the disposable implantation guide track.

DETAILED DESCRIPTION OF PREFERRED EMBODIMENT

Figure 1:
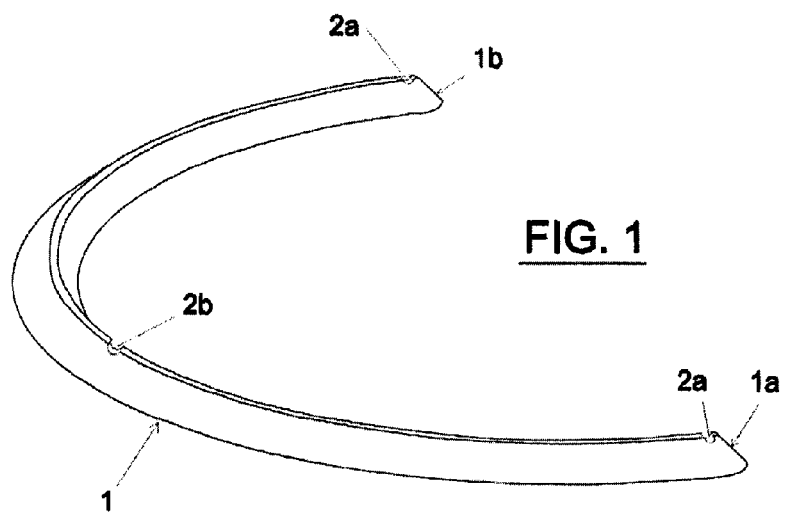
FIG. 1 shows a schematic view from above of the intrastromal segment construed in agreement with the principles of the present invention.

Only and exactly as it has been discussed in the preceding, a detailed description of the template for preferred implementation of the invention shall be carried out in the following with the aid of annexed drawings, in which identical numerical references are be used to designate the corresponding parts of their equivalents. Thus FIG. 1 gives a schematic view, in perspective, of an example of a segment construed according to the invention, indicated in general by the numerical reference 1. In the represented example, the segment consists in a longitudinal arched body from a transverse trapezoidal section with invariable radius, whose points 1a and 1b are delimited by a noticeably smoothed surface to facilitate insertion, inclined toward the inside in an ascending direction (according to the position of the Figure title) and which diminishes in width to ascend by virtue of the trapezoidal section furnished to the body of the segment.

It will be understood that in whatever case, the trapezoidal configuration chosen for the example from FIG. 1 constitutes only one example of implementation, given that the segment could equally take up any one of the customary configurations mentioned in the preceding.

FIG. 1 allows one to see that the intrastromal segment 1 is devoid of any communicating orifice between the bases of the trapezoids in near its ends, as occurs in the case of intrastromal segments implanted using previous techniques that are the source of so many of the disadvantages described. In contrast, segment 1 of the present invention displays superior marks at end and central positions relative to the narrow base of the trapezoid (that is to say the upper base according to the FIG. 1), These marks consist of radial grooves such that the end grooves are labelled with numerical reference 2a and the central groove is labelled with numerical reference 2b. The end marks 2a, according to what we have said, can be used for the smooth insertion of the intrastromal segment into the corneal tunnel, while the central mark 2b constitutes an exact reference point for tracking at any moment the evolution of the insertion and for knowing when it has reached the proper location for implantation.

Again it is important to mention that the preferred implementation of segment 1 envisages the formation of three marks 2a, 2b, but this number of marks should not be understood as restrictive, given that it can vary according to each concrete need.

Figure 2:
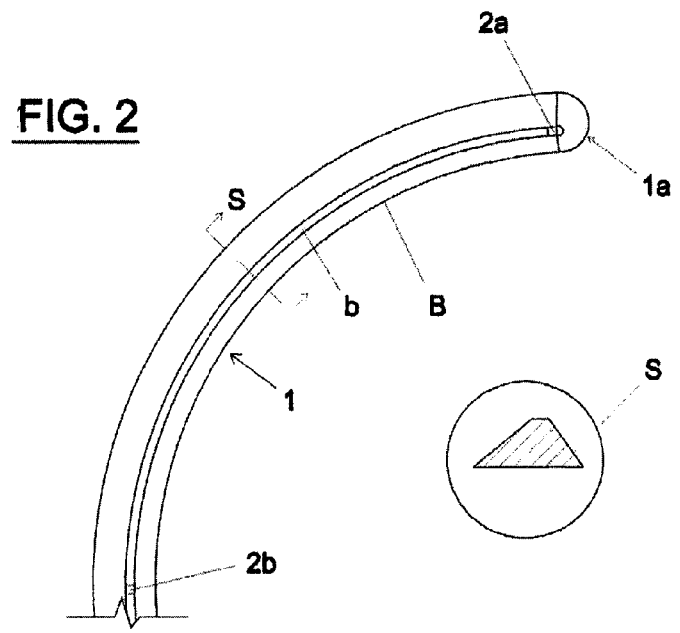
FIG. 2 is a representation from the upper plane that shows a longitudinal portion of in greater detail (in particular the cross-section of the longitude) of the segment shown in FIG. 1.

FIG. 2 gives an upper plane representation of an intrastromal semi-segment from FIG. 1, that is, a portion of the segment that corresponds approximately to one half of the longitude of the segment 1. This representation permits one to understand how the minor base "b" that occupies the upper position in the Figure, is lightly displaced toward the inside with respect to the longitudinal section of the major base "B", thanks to the trapezoidal form in transverse section of segment 1, clearly visible in the detail labelled as "S" in FIG. 2. The radius of the arched segment 1 is uniform but can vary according to necessities arising from various practical situations, as can the rest of the dimensions of segment 1. Examples of these variations in the distinct possibilities of implementation are graphically shown in representations (a) and (b) in FIG. 3. Each one of the aforementioned representations from FIG. 3 illustrates a group of intrastromal segments seen schematically from one of its ends, so that those corresponding to group (a), indicated by numerical reference 1 present a width dimension in its respective upper and lower bases b-B that is identical for all the segments, but which can vary progressively with respect to their relative height. For its part, segments of group (b) are equal with respect to the dimension of their upper and lower bases b'-B', and also vary progressively with respect to their relative height; nevertheless, the width dimension of group (b) comparative to the segments of group (a), is appreciably less than that of the latter. These variations clearly illustrate the possibilities of adaptation of the dimensions of the segments to distinct practical necessities, with independence from the configuration they assume in transverse section.

Now making reference to FIG. 4 it is possible to discern the invention segment inserted in disposable guide track 3, construed in agreement with the invention, to facilitate the correct positioning of the implant segment into the patient's cornea. Guide track 3 is configured in the manner of "C", composed of a central section 3a, from which emerge two end sections 2b that are inclined toward the inside with respect to the central section 3a, forming sharp angles with this last. The segment of implant 1 is connected to guide track 3 by positioning of its widest area (major base "b") on the inside of guide track 3, supported over the internal face of the central section 3a, without possibility of separation or accidental disconnection from the guide track because the greater width dimension of base B with respect to the open portion made accessible by the distance of the separation between both end sections 3b of the guide track prevents it. In this way the segment is made ready for implantation, without possibility of losses or incorrect positioning, having been inserted directly from guide track 3 into the patient's cornea, thus considerably facilitating the handling of the assembly.

It is not considered necessary to elaborate further the content of the present description for an expert in the subject to understand its extent and the advantages that are to be had from it.

The preceding descriptions notwithstanding, and given that the description found here refers solely to an example of implementation of the invention's object, it will be understood that in its essentials, it is possible to introduce multiple variations in detail, equally protected, that in particular are capable of affecting features such as the form, size or manufacturing materials of the assembly or of its parts, or whatever others that might not alter the essentials of the invention delimited solely through the scope of the claims that follow.

The invention claimed is:

1. An intrastromal segment used as an implant for insertion into the patient's cornea consisting of:
    a longitudinal arched body with a given radius and having a cross-sectional configuration that is one of triangular, trapezoidal, hexagonal or oval;
    the body having two smoothed ends having a rounded surface inclined from a base toward the narrowest part of the cross-sectional configuration; and
    several marks located on the body that include at least first two radial grooves positioned near both ends and a second radial groove positioned at a central position on the body,
    wherein the at least two radial grooves are arranged to aid in the handling and insertion of the body into an intrastromal tunnel formed in the patient's cornea, and the second radial groove is arranged so that, when positioning the body inside the intrastromal tunnel, an exact point of the cornea where the body is to be placed can be indicated.

2. The intrastromal segment according to claim 1, further comprising a disposable guide track, which, in general, adopts a C-shaped configuration, with end portions bent towards an interior until forming with a central portion respective acute angles,
    wherein the body is housed with the base resting on an inner face of the central portion, where the body is inserted, in the correct position directly in the intrastromal tunnel of the patient's cornea.

3. The intrastromal segment according to claim 1, wherein, for different patients, dimensions of the cross-sectional configuration are different.

4. The intrastromal segment according to claim 3, wherein each different cross-sectional configuration has a same dimension for the base and the narrowest part.

5. The intrastromal segment according to claim 1, wherein, for different patients, dimensions of the cross-sectional configuration are the same.

6. The intrastromal segment according to claim 1, wherein, for different patients, the radius of the body is different.

7. The intrastromal segment according to claim 1, wherein, for different patients, the radius of the body is the same.

8. An intrastromal segment used as an implant for insertion into the patient's cornea comprising:
    a longitudinal arched body with a given radius and having a cross-sectional configuration that is one of triangular, trapezoidal, hexagonal or oval;
    the body having two smoothed ends having a rounded surface inclined from a base toward the narrowest part of the cross-sectional configuration; and
    several marks located on the body that include at least first two radial grooves positioned near both ends and a second radial groove positioned at a central position on the body, wherein the at least two radial grooves are arranged to aid in the handling and insertion of the body into an intrastromal tunnel formed in the patient's cornea, and the second radial groove is arranged so that, when positioning the body inside the intrastromal tunnel, an exact point of the cornea where the body is to be placed can be indicated.

* * * * *